(12) United States Patent
Song et al.

(10) Patent No.: US 6,268,352 B1
(45) Date of Patent: Jul. 31, 2001

(54) PROMOTERS OF NEURAL REGENERATION

(75) Inventors: Hong-jun Song; Mu-Ming Poo; Guo-li Ming, all of La Jolla; Marc Tessier-Lavigne; Zhigang He, both of San Francisco, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/145,820

(22) Filed: Sep. 2, 1998

(51) Int. Cl.[7] .......................... A61K 31/70; A61K 31/40; A61K 31/33
(52) U.S. Cl. ............................. 514/47; 514/42; 514/48; 514/183; 514/192; 514/220; 514/211.12; 514/227.2; 514/248; 514/263; 514/274; 514/376; 514/423; 514/453; 435/375
(58) Field of Search ................... 514/42, 47, 48, 514/183, 192, 220, 211.12, 227.2, 263, 274, 248, 376, 423, 453; 435/375

(56) References Cited

U.S. PATENT DOCUMENTS 5,656,605 * 8/1997 Hansson et al. ..................... 514/21
6,043,224 * 3/2000 Lee et al. ........................... 514/26

OTHER PUBLICATIONS

Genain, C.P. et al. Prevention of Autoimmune Demyelination in Non–Human Primates by a cAMP–Specific Phosphodiesterase Inhibitor. PNAS USA Apr. 1995, vol. 92, pp. 3601–3605, see abstract.

Rydel et al. *Proc. Natl. Acad. Sci. USA* Feb. 1988, 85, 1257–61.*

* cited by examiner

*Primary Examiner*—Kathleen Kahler Fonda
(74) *Attorney, Agent, or Firm*—Richard Aron Osman

(57) ABSTRACT

The invention provides methods and compositions for promoting neural cell growth and/or regeneration. The general methods involve contacting with an activator of a cyclic nucleotide dependent protein kinase a neural cell subject to growth repulsion mediated by a neural cell growth repulsion factor. The activator may comprise a direct or an indirect activator of the protein kinase; the repulsion factor typically comprises one or more natural, endogenous proteins mediating localized repulsion or inhibition of neural cell growth; and the target cells are generally vertebrate neurons, typically injured mammalian neurons. The subject compositions include mixtures comprising a neural cell, an activator of a cyclic nucleotide dependent protein kinase and a neural cell growth repulsion factor.

64 Claims, 9 Drawing Sheets

PROMOTERS OF NEURAL REGENERATION

The research carried out in the subject application was supported in part by NIH grant NS22764. The government may have rights in any patent issuing on this application.

INTRODUCTION

1. Field of the Invention

The field of this invention is nerve cell growth regulation.

2. Background

The failure of the adult central nervous system (CNS) to regenerate after injury is a major clinical problem, affecting some 200,000 people in the United States alone. Despite intensive research, an effective approach in promoting significant regeneration of CNS nerve fibers remains lacking. The inability of CNS to regenerate is partly due to inhibitory factors associated with myelin, a cellular structure surrounding the nerve fibers.

There are currently few effective methods that can promote significant nerve regeneration of severed or damaged nerve fibers. A number of endogenous molecules are known to modulate neural cell growth (1). These factors may exert either attractive or repulsive action on the extension of axonal growth cones (1,2). Experiments in mammals have shown that blocking of some of the inhibitory factors by antibodies could promote regeneration of severed axons in the spinal cord and lead to functional recovery of limb movements.

Recent reports have shown that attractive responses to netrins, mediated by the DCC/UNC-40 family of proteins, can be converted to repulsion by coexpression of proteins of the UNC-5 family (3). In addition, attractive effects of brain-derived neurotrophic factor (BDNF) and netrin-1 on Xenoputs spinal neurites in culture can be converted to repulsion by inhibition of protein kinase A activity (4, 5). We disclose here the opposite phenomenon: that by specific pharmacological manipulations, the action of neural cell inhibitory (or repulsive) factors can be reversed. Such pharmacological treatments change the inhibitory nature of those inhibitory factors into supportive factors and thus promote nerve regeneration.

SUMMARY OF THIE INVENTION

We have found that the action of many protein factors that either inhibit or promote nerve growth are mediated through two general mechanisms. Factors such as neurotrophins including brain-derived neurotrophic factor (BDNF) and neurotrophin 3 (NT-3) as well as certain netrins can promote nerve growth in vitro. Nerve fibers grow towards these factors when presented as a localized source. On the other hand, factors such as Semaphorin III, myelin-associated glycoprotein (MAG) and purified myelin, cause collapse of the nerve terminal and block nerve growth. When these factors present as a localized source, nerve fibers grow away from these factors. We have further found that the inhibitory or repulsive effects of the latter factors can be reversed by pharmacological treatments that activate cyclic nucleotide dependent protein kinases, e.g. by increasing the level of cyclic nucleotides, cAMP and cGMP. In addition, we found the action of protein factors that promote nerve growth, e.g. BDNF and NT-3, can also be enhanced by these cyclic nucleotides. Thus by pharmacological interventions that elevate the cyclic nucleotide levels, we are able to help nerve regeneration associated with injuries of the nervous system.

Accordingly, the invention provides methods and compositions for promoting neural cell growth and/or regeneration. The general methods involve contacting with an activator of a cyclic nucleotide dependent protein kinase a neural cell subject to growth repulsion mediated by a neural cell growth repulsion factor. The activator may comprise a direct or indirect activator of the protein kinase, including cyclic nucleotide analogs, activators of a cyclic nucleotide cyclase, NO inducers, inhibitors of a cyclic nucleotide phosphodiesterase, etc. The repulsion factor typically comprises one or more natural, endogenous proteins mediating localized repulsion or inhibition of neural cell growth. Examples include neural cell guidance proteins such as semaphorins, CNS myelin fractions or components thereof such as MAG, etc. The target cells are generally vertebrate neurons, typically injured mammalian neurons in situ. The subject compositions include mixtures comprising a neural cell, an activator of a cyclic nucleotide dependent protein kinase and a neural cell growth repulsion factor.

The total number of neurons examined is shown in parenthesis. '*': Significantly different from the data set at zero concentration (p<0.05, Kruskal-Wallis test). (B) Correlation of turning angles induced by a Sema III gradient in normal medium (first turn) and in medium containing 8-br-cGMP (second turn) for the same neuron. The line represents best linear fit of the data (r=−0.88, p=0.02).

FIGS. 2A–2D. Growth cone turning in a gradient of Sema III. (A) Effects of manipulating cGMP-dependent activities. Angular positions of all growth cones at the end of the one-hour exposure to a Sema III gradient (50 $\mu$g/ml in the pipette) are shown in a cumulative distribution plot for the following conditions: normal medium, medium containing 8-br-cGMP (100 $\mu$M), Sp-cGMPS (10 $\mu$M), Protoporphyrin-9 (PP-9, 10 $\mu$M), S-Nitroso-N-acetylpenicillamine (SNAP, 300 $\mu$M), and Rp-cGMPS (10 $\mu$M). Isolated symbols along the abscissa are median values for corresponding data shown above. (B) Effects of manipulating cAMP-dependent activities. Shown are distributions of turning angles for the following conditions: normal culture medium, medium containing 8-br-cGMP (100 $\mu$M), Rp-cAMPS (20 $\mu$M), Sp-cAMPS (20 $\mu$M), both 8-br-cGMP (100 $\mu$M) and Rp-cAMPS (20 $\mu$M), or both 8-br-cGMP (100 $\mu$M) and Sp-cAMPS (20 $\mu$M). (C) Distribution of turning angles in the absence or presence of $\alpha$-28 (20 $\mu$g/ml) in normal medium and in medium containing 8-br-cGMP (100 $\mu$M). '*': significantly different (p<0.01, Kolmogorov-Smirnov test). (D) Effects of reducing $[Ca^{2+}]_o$ on turning responses in a Sema III gradient. Due to increased growth rate, the turning in 1 $\mu$M $[Ca^{2+}]_o$ was assayed 30 min after the onset of the gradient. Distribution of turning angles in normal (1 mM) or low (1 $\mu$M) $Ca^{2+}$ medium in the absence or presence of 8-br-cGMP (100 $\mu$M). '‡': not significantly different (p>0.2, Kolmogorov-Smirnov test).

Figure 3:
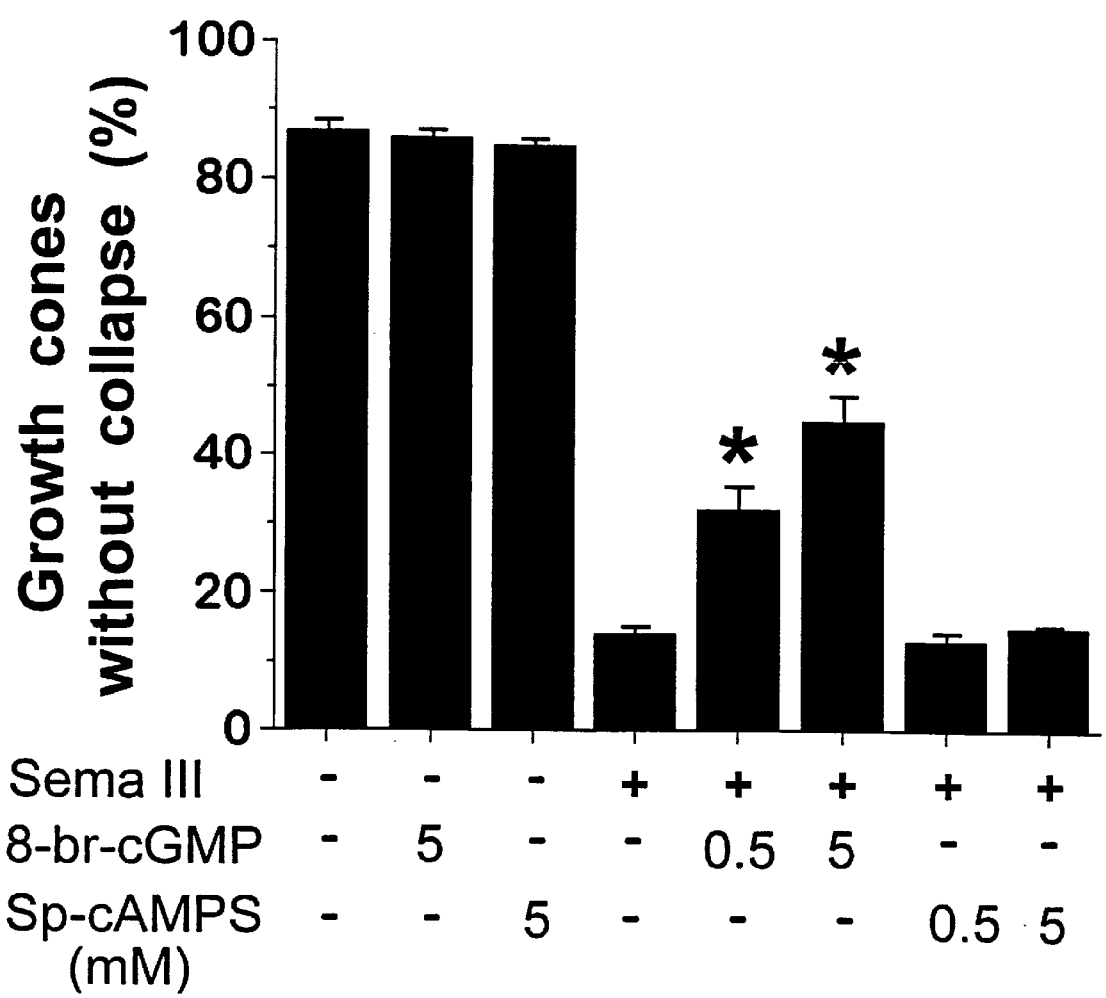

FIG. 3. Percentage of intact growth cones from the explants treated with cyclic nucleotides and/or Sema III. Error bars refer to SEM. '*': Significantly different from the set without pretreatment with 8-br-cGMP and Sp-cAMPS (P<0.001, t-test)

FIGS. 4A–4D. (A) Effects of manipulating cyclic nucleotide levels on turning induced by a rMAG gradient (150 $\mu$g/ml in the pipette) in normal medium, in medium containing 8-br-cGMP (100 μM) or Sp-cAMS (20 μM), and by heat-inactivated rMAG in normal medium. Results from the latter were significantly different from all three other groups (p<0.01, Kolmogorov-Smirnov test). (B) Effects of reducing $[Ca^{2+}]_o$ on turning responses induced by rMAG. Distribution of turning angles in normal (1 mM) or low (1 μM) $Ca^{2+}$ medium in the absence or presence of Sp-cAMPS (20 μM). '*': Significantly different (p<0.05, Kolmogorov-Smirnov test). (C) Turning responses induced by a gradient of netrin-1 (5 μg/ml in the pipette) (5), in normal medium and in medium containing Rp-cGMPS (10 gM), 8-br-cGMP (100 μM), Rp-cAMPS (20 μM), or both Rp-cAMPS (20 μM) and 8-br-cGMP (100 μM). Also shown is the control distribution of turning angles observed when the pipette contained only culture medium (no gradient), which is significantly different from all other data sets (p<0.05, Kolmogorov-Smirnov test). (D) Turning induced by a NT-3 gradient (50 μ/ml in the pipette) in normal medium and in medium containing Rp-cAMPS (20 μM) or Rp-cGMPS (10 μM), or in medium containing 1 μM $Ca^{2+}$. All data sets were significantly different from the no gradient control (p<0.05, Kolmogorov-Smirmov test).

Figure 5:
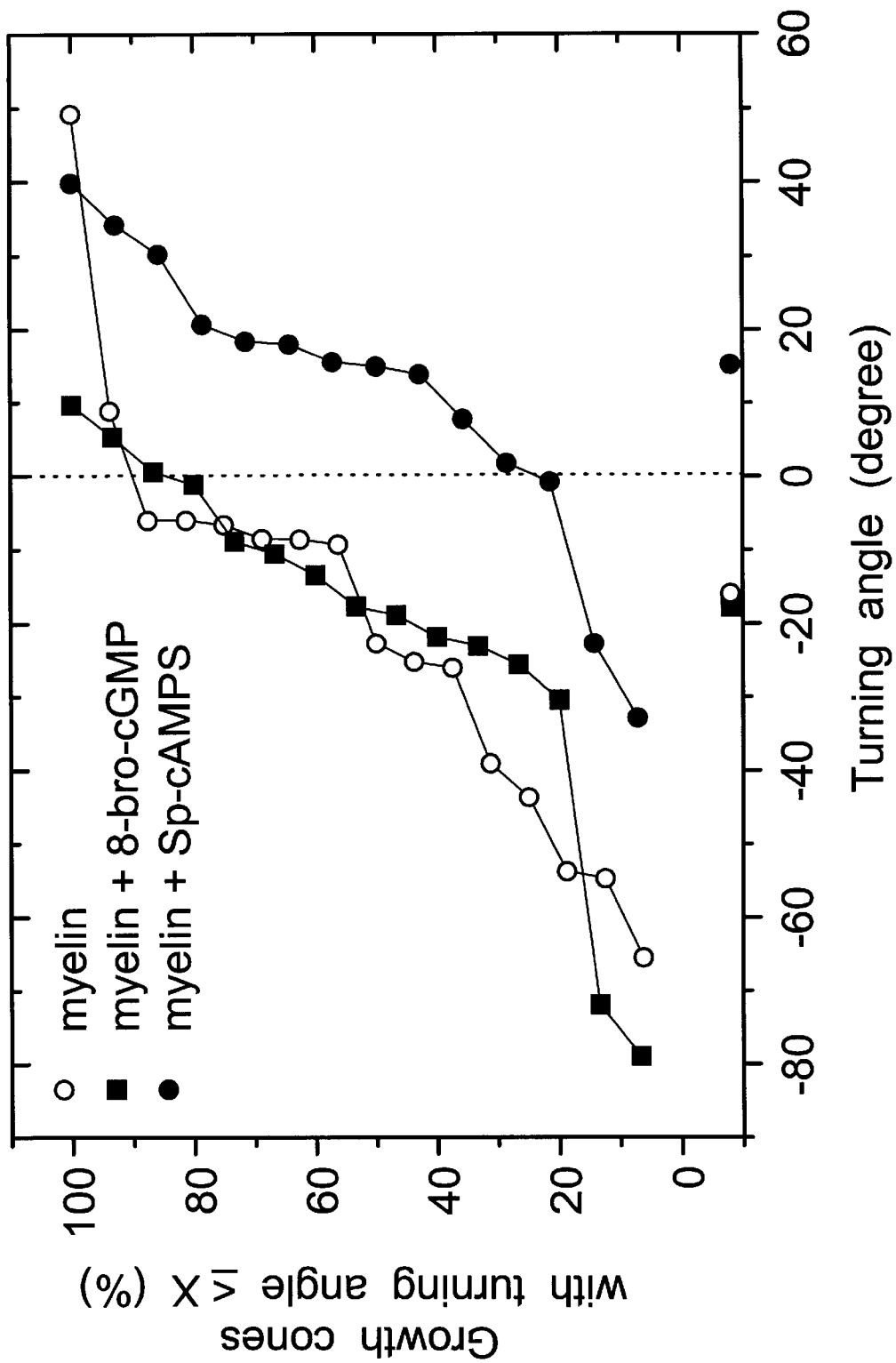

FIG. 5. Growth cone turning induced by purified myelin. A gradient of purified myelin (25 μg/ml in the pipette) was applied in normal culture medium (open circles), in medium containing Sp-cAMPS (20 μM, solid circles), or 8-br-cGMP (100 μM, solid squares). Isolated symbols along the abscissa are median values for corresponding data shown above.

Figure 6A:
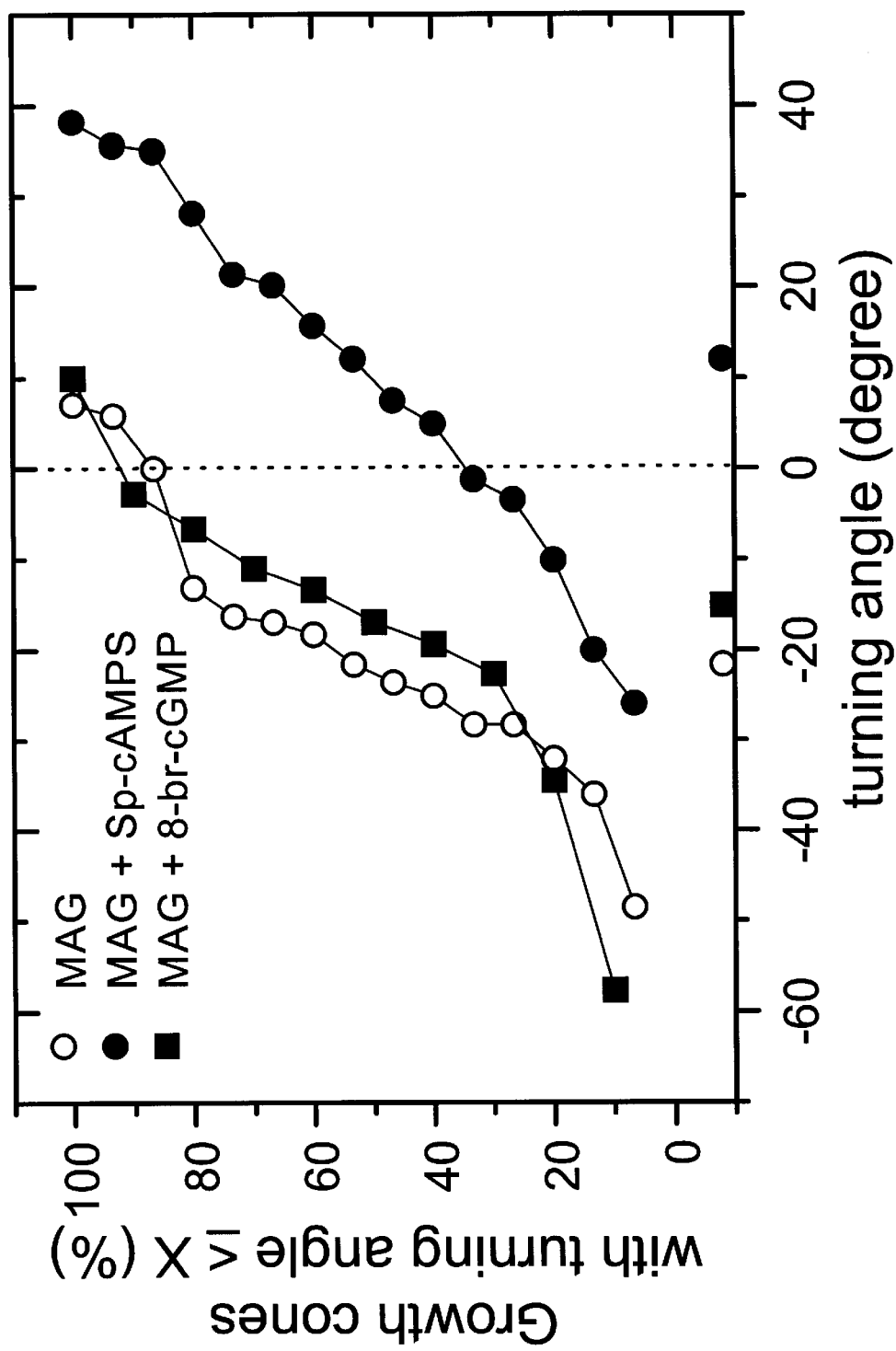
Figure 6B:
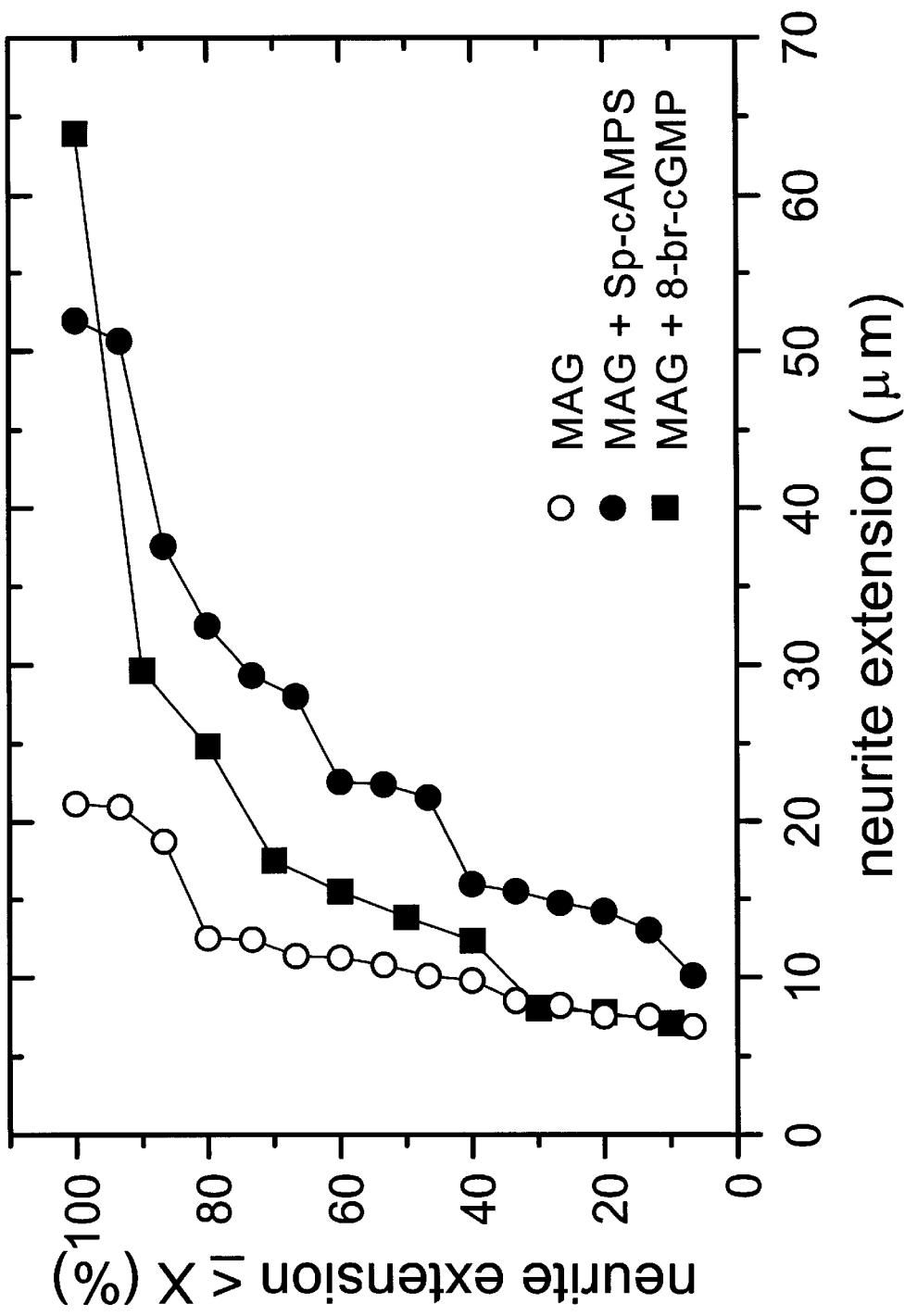

FIGS. 6A, 6B. Effects of purified myelin-associated glycoprotein (MAG) on growth cones of Xenopus spinal neurons. A gradient of purified MAG (150 μg/ml in the pipette) was applied in normal culture medium (open circles), in medium containing Sp-cAMPS (20 μM, solid circles), or in medium containing 8-br-cGMP (100 μM, solid squares). (A) Shown are distributions of turning angles under different conditions. Isolated symbols along the abscissa are median values for corresponding data shown above. (B) Shown are distributions of net neurite extension in the gradient under different conditions.

Figures 7A, 7B:
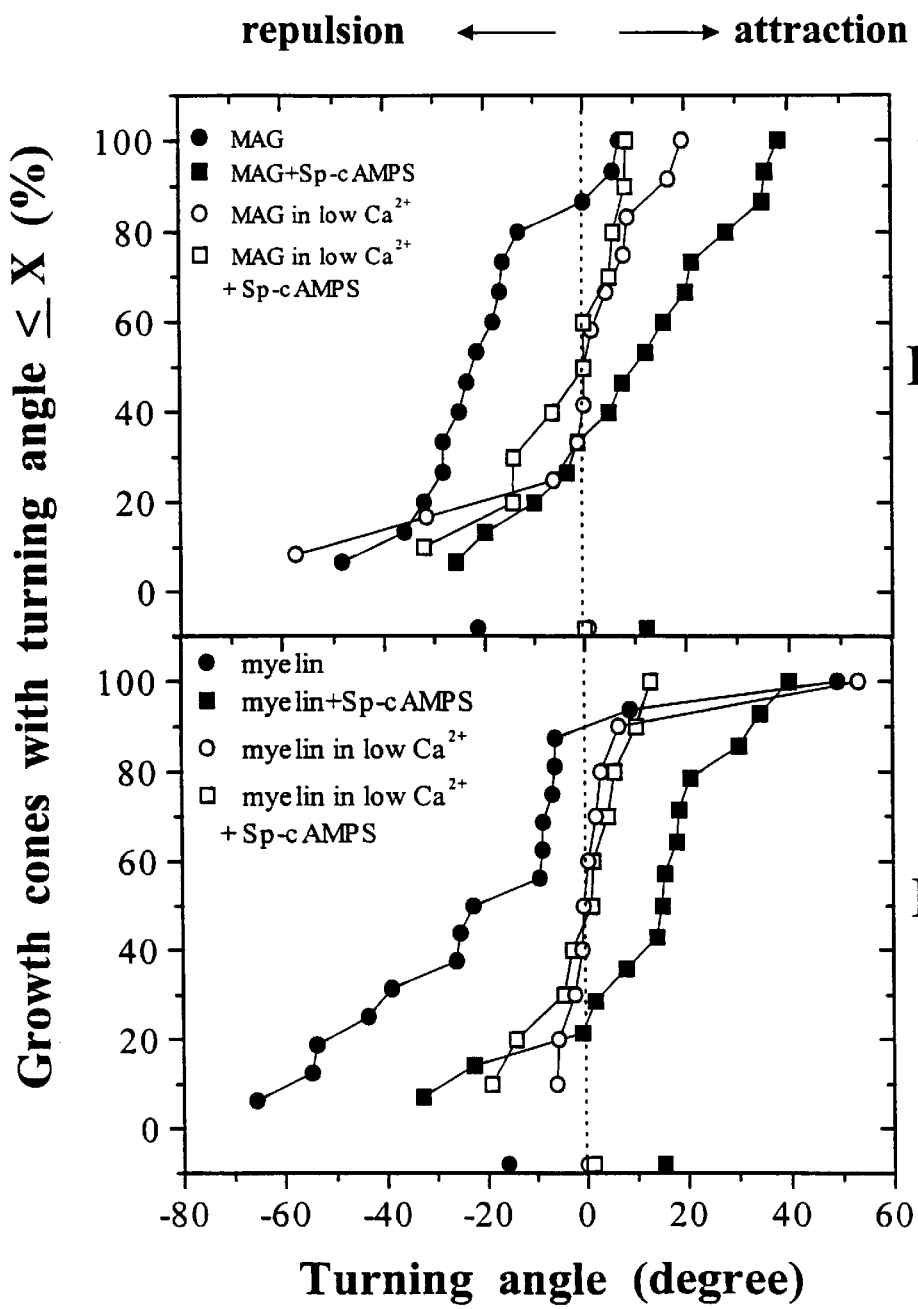

FIGS. 7A, 7B. Effects of reducing external $Ca^{2+}$. (A) Purified MAG-induced turning depends on $[Ca^{2+}]_o$. Shown are distributions of turning angles in normal medium in the absence (solid circles) or presence of Sp-cAMPS (20 μM, solid squares), and in medium containing 1 μM $[Ca^{2+}]_o$ in the absence (open circles) or presence of Sp-cAMPS (20 μM, open squares), respectively. Isolated symbols along the abscissa are median values for corresponding data shown above. (B) Purified myelin-induced turning depends on $[Ca^{2+}]_o$. Shown are distributions of turning angles in normal medium in the absence (solid circles) or presence of Sp-cAMPS (20 μM, solid squares), and in medium containing 1 μM $[Ca^{2+}]_o$ in the absence (open circles) or presence of Sp-cAMPS (20 μM, open squares), respectively.

DETAILED DESCRIPTION OF THE INVENTION

The general methods involve contacting with an activator of a cyclic nucleotide dependent protein kinase a neural cell subject to growth repulsion mediated by a neural cell growth repulsion factor. Preferred activators enhance the activity of at least one of PKA or PKG. A wide variety of direct and indirect activators of cyclic nucleotide dependent protein kinases are known in the art, or readily identified in assays such as immuno, kinase and cell based assays. Indirect activators are agents which increase the activity of the protein kinase without directly interacting with the kinase, and include any agent which increases the functional activity of the corresponding cyclic nucleotide (e.g. by increasing its synthesis, increasing its availability, decreasing its degradation, etc.). Exemplary activators include cyclic nucleotide analog agonists, activators of cyclic nucleotide cyclases, NO inducers, inhibitors of cyclic nucleotide phosphodiesterases, drugs such as KT5720, etc. Additional activators are readily made by screening candidate agents for activation of the targeted protein kinase, inhibition of a targeted phosphodiesterase (e.g. cAMP or cGMP phosphodiesterase), activation of a targeted cyclase (e.g. guanylate or adenylate cyclase), etc. in conventional in vitro or cell based assays.

The repulsion factor typically comprises one or more natural, endogenous agents mediating localized repulsion or inhibition of the targeted neural cell growth, which repulsion or inhibition is reversible by increasing the activity of a cyclic nucleotide dependent protein kinase in the cell. Such factors are generally present at the site of neuronal cells in situ, particularly at the cite of CNS axons, and provide an endogenous inhibition to nerve cell growth and/or regeneration. A wide variety of such factors are known or are readily identified in cell based assays, such as described herein. Exemplary agents capable of acting as repulsion factors include neural cell guidance proteins such as some semaphorins, netrins, CNS myelin fractions or components thereof such as MAG, etc.

The target cells are generally vertebrate neurons, typically injured mammalian neurons in situ. A wide variety of methods may be used to effect the contacting of the cell with the activator. For example, for CNS administration, a variety of techniques are available for promoting transfer of therapeutic agents across the blood brain barrier including disruption by surgery or injection, drugs which transiently open adhesion contact between CNS vasculature endothelial cells, and compounds which facilitate translocation through such cells. The compositions may also be amenable to direct injection or infusion, intraocular administration, or within/ on implants e.g. fibers such as collagen fibers, in osmotic pumps, grafts comprising appropriately transformed cells, etc.

In a preferred embodiment, the activator is delivered locally and its distribution is restricted. For example, a particular method of administration involves coating, embedding or derivatizing fibers, such as collagen fibers, protein polymers, etc. with therapeutic agents, see also Otto et al. (1989) J Neuroscience Research 22, 83–91 and Otto and Unsicker (1990) J Neuroscience 10, 1912–1921. Another particular embodiment is adapted from treatment of spinal cord injuries, e.g. Schulz M K, et al., Exp Neurol. February; 1998 149(2): 390–397; Guest J D, et al., J Neurosci Res. Dec. 1, 1997 50(5): 888–905; Schwab M E, et al., Spinal Cord. July; 1997 35(7): 469–473; Tatagiba M, et al., Neurosurgery. March; 1997 40(3): 541–546. For example, the subject compositions improve corticospinal tract (CST) regeneration following thoracic spinal cord injury by promoting CST regeneration into human Schwann cell grafts in the methods of Guest et al. (supra). For these data, the human grafts are placed to span a midthoracic spinal cord transection in the adult nude rat, a xenograft tolerant strain. Activators (see Table 1) incorporated into a fibrin glue are placed in the same region. Anterograde tracing from the motor cortex using the dextran amine tracers, Fluororuby (FR) and biotinylated dextran amine (BDA), are performed. Thirty-five days after grafting, the CST response is evaluated qualitatively by looking for regenerated CST fibers in or beyond grafts and quantitatively by constructing camera lucida composites to determine the sprouting index (SI), the position of the maximum termination density (MTD) rostral to the GFAP-defined host/graft interface, and the longitudinal spread (LS) of bulbous end terminals. The latter two measures provide information about axonal die-back. In control animals (graft only), the CST do not enter the SC graft and undergo axonal die-back. As shown in Table 1, the activators dramatically reduce axonal die-back and cause sprouting.

TABLE I

In Vivo Neuronal Regenration with Exemplary Activator Formulations

| Activator | Formulation | Reduced Die-Back | Promote Sprouting |
|---|---|---|---|
| 1. Forskolin | 5 uM | ++++ | ++++ |
| 2. 7β-Deaceyl-7β-[γ-(morpholino)butyryl]-forskolin | 5 uM | ++++ | ++++ |
| 3. 6β-[β'-(Piperidino)-propionyl]-forskolin | 5 uM | ++++ | ++++ |
| 4. 3-Isobutyl-1-methylxanthine (IBMX) | 25–100 uM | ++++ | ++++ |
| 5. Rolipram | 2 uM | ++++ | ++++ |
| 6. 8-bromo-cAMP | 100 uM | ++++ | ++++ |
| 7. 8-chloro-cAMP | 100 uM | ++++ | ++++ |
| 8. 8-(4-chlorophenylthio)-cAMP | 100 uM | ++++ | ++++ |
| 9. Dibutyryl-cAMP | 100 uM | ++++ | ++++ |
| 10. Dioctanoyl-cAMP | 100 uM | ++++ | ++++ |
| 11. Sp-cAMPS | 20 uM | ++++ | ++++ |
| 12. Sp-8-bromo-cAMPS | 20 uM | ++++ | ++++ |
| 13. 8-br-cGMP | 100 uM | ++++ | ++++ |
| 14. 8-(4-chlorophenylthio)-cGMP | 100 uM | ++++ | ++++ |
| 15. Dibutyryl-cGMP | 100 uM | ++++ | ++++ |
| 16. Glyco-SNAP-1 | 300 uM | ++++ | ++++ |
| 17. Glyco-SNAP-2 | 300 uM | ++++ | ++++ |
| 18. S-Nitroso-N-acetylpenicillamine | 300 uM | ++++ | ++++ |
| 19. NOC-18 | 100 uM | ++++ | ++++ |
| 20. NOR-3 | 100 uM | ++++ | ++++ |
| 21. Protoporphyrin-9 | 10 uM | ++++ | ++++ |

In another demonstration of in vivo therapeutic activity, the subject activators are incorporated in the implantable devices described in U.S. Pat No. 5,656,605 and tested for the promotion of in vivo regeneration of peripheral nerves. Prior to surgery, 18 mm surgical-grade silicon rubber tubes (I.D. 1.5 mm) are prepared with or without guiding filaments (four 10-0 monofilament nylon) and filled with test compositions comprising the activators of Table 1. Experimental groups consist of: 1. Guiding tubes plus Biomatrix 1™ (Biomedical Technologies, Inc., Stoughton, Mass.); 2. Guiding tubes plus Biomatrix plus filaments; 3–23. Guiding tubes plus Biomatrix 1™ plus activators 1–21 of Table 1 (supra).

The sciatic nerves of rats are sharply transected at midthigh and guide tubes containing the test substances with and without guiding filaments sutured over distances of approximately 2 mm to the end of the nerves. In each experiment, the other end of the guide tube is left open. This model simulates a severe nerve injury in which no contact with the distal end of the nerve is present.

After four weeks, the distance of regeneration of axons within the guide tube is tested in the surviving animals using a functional pinch test. In this test, the guide tube is pinched with fine forceps to mechanically stimulate sensory axons. Testing is initiated at the distal end of the guide tube and advanced proximally until muscular contractions are noted in the lightly anesthetized animal. The distance from the proximal nerve transection point is the parameter measured. For histological analysis, the guide tube containing the regenerated nerve is preserved with a fixative. Cross sections are prepared at a point approximately 7 mm from the transection site. The diameter of the regenerated nerve and the number of myelinated axons observable at this point are used as parameters for comparison.

Measurements of the distance of nerve regeneration document the therapeutic effect of groups 3–23. Similarly, plots of the diameter of the regenerated nerve measured at a distance of 7 mm into the guide tube as a function of the presence or absence of one or more activators of the device demonstrate a similar therapeutic effect of all 21 activators tested. No detectable nerve growth is measured at the point sampled in the guide tube with the matrix-forming material alone. The presence of guiding filaments plus the matrix-forming material (no activator) induces only very minimal regeneration at the 7 mm measurement point, whereas dramatic results, as assessed by the diameter of the regenerating nerve, are produced by the device which consisted of the guide tube, guiding filaments and activator compositions. Finally, treatments using guide tubes comprising either a matrix-forming material alone, or a matrix-forming material in the presence of guiding filaments, result in no measured growth of myelinated axons. In contrast, treatments using a device comprising guide tubes, guiding filaments, and matrix containing activator compositions consistently result in axon regeneration, with the measured number of axons being increased markedly by the presence of guiding filaments.

The amount of activator administered depends on the activator, formulation, route of administration, etc. and is generally empirically determined. For example, with cyclic nucleotide activators delivered locally in a solid matrix or semi-solid phase, the administered dose is typically in the range of about 2 mg up to about 2,000 mg, although variations will necessarily occur depending on the target, the host, and the route of administration, etc,.

In one embodiment, the invention provides the subject activators combined with a pharmaceutically acceptable excipient suitable for contacting target neuronal cells in situ, such as CNS administration, including as sterile saline or other medium, gelatin, an oil, etc. to form pharmaceutically acceptable compositions. The compositions and/or compounds may be administered alone or in combination with any convenient carrier, solid or semi-solid matrix, diluent, etc. and such administration may be provided in single or multiple dosages. Useful carriers and matrices include solid, semi-solid or liquid media including water and non-toxic organic solvents. In another embodiment, the invention provides the subject compounds in the form of a pro-drug, which can be metabolically converted to the subject compound by the recipient host. A wide variety of pro-drug formulations are known in the art. The compositions may be provided in any convenient form including tablets, capsules, fibers, guides, osmotic pumps, etc. (see, e.g. U.S. Pat. Nos. 5,656,605; 5,660,849 and 5,735,863 for delivery systems particularly suited for CNS administration). As such the compositions, in pharmaceutically acceptable dosage units or in bulk, may be incorporated into a wide variety of containers and materials. For example, dosage units may be included in a variety of containers including microcapsules, pumps, fibers, etc.

The compositions may be advantageously combined and/or used in combination with other therapeutic or prophylactic agents, different from the subject compounds. In many instances, administration in conjunction with the subject compositions enhances the efficacy of such agents. For example, the compounds may be advantageously used in conjunction with other neurogenic agents, neurotrophic factors, growth factors, anti-inflammatories, antibiotics etc.; and mixtures thereof, see e.g. Goodman & Gilman's The Pharmacological Basis of Therapeutics, 9th Ed., 1996, McGraw-Hill, esp. Chabner et al., Antineoplastic Agents at pp. 1233.

The subject compositions include ex vivo mixtures comprising a neural cell, an activator of a cyclic nucleotide dependent protein kinase and a neural cell growth repulsion factor. Such mixtures may be used in in vitro screens for identifying suitable activators, optimizing formulations, delivery concentrations, etc., etc.

The following experimental section and examples are offered by way of illustration and not by way of limitation.

EXAMPLES

Figure 1A:
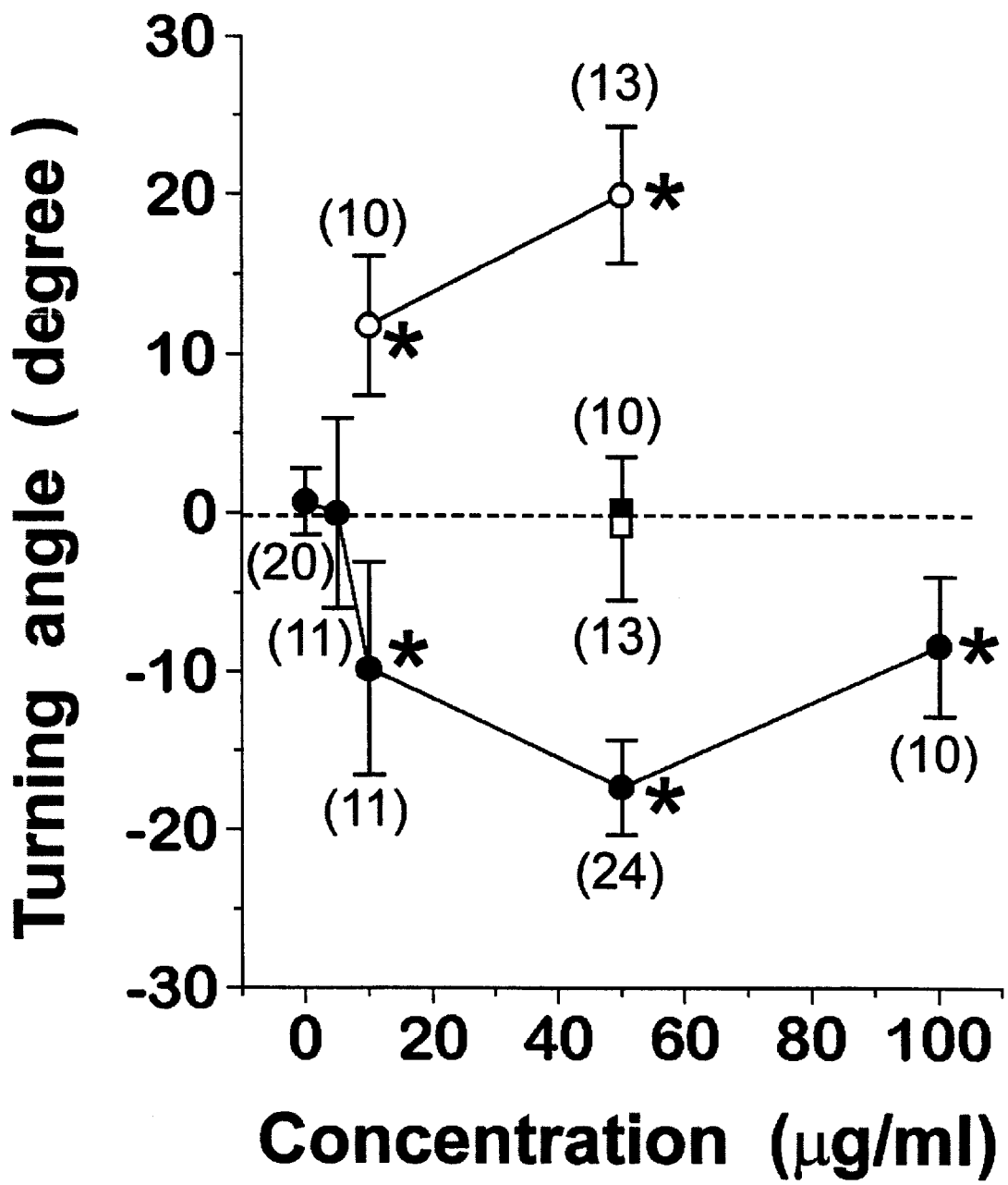
FIG. 1A, 1B. (A) The dependence of turning responses on the Sema III concentration in the pipette. Turning angles (mean±SEM) (8) in normal medium (filled symbols) and in medium containing 8-br-cGMP (100 $\mu$M, open symbols), and for heat-inactivated Sema III (sqaures).

Collapsin-1/Semaphorin III/D (Sema III), a diffusible member of the semaphorin family can repel or cause collapse of growth cones in culture (6). Defects in Sema III knock-out mice suggest that Sema III creates exclusion zones for axons or drives axonal fasciculation through surround repulsion (7). We analyzed the effect of a microscopic gradient of Sema III on growth cones of the cultured Xenopus spinal neuron (8). Sema III-containing saline was applied in pulses from a micropipette positioned 100 μm from the center of the growth cone and at a 45° angle with respect to the original direction of neurite extension. Most growth cones grew away from the pipette. The repulsive response was dose-dependent with a minimal response occurring at an effective concentration of about 10 ng/ml at the growth cone (8). Heat-inactivated Sema III was ineffective (FIG. 1A). The repulsive turning was initiated by active protrusion of filopodia in the direction away from the pipette, with no obvious growth cone collapse during the turning process (9). The rate of neurite extension was unaffected by the presence of the Sema III gradient.

Figures 2A, 2B, 2C, 2D:
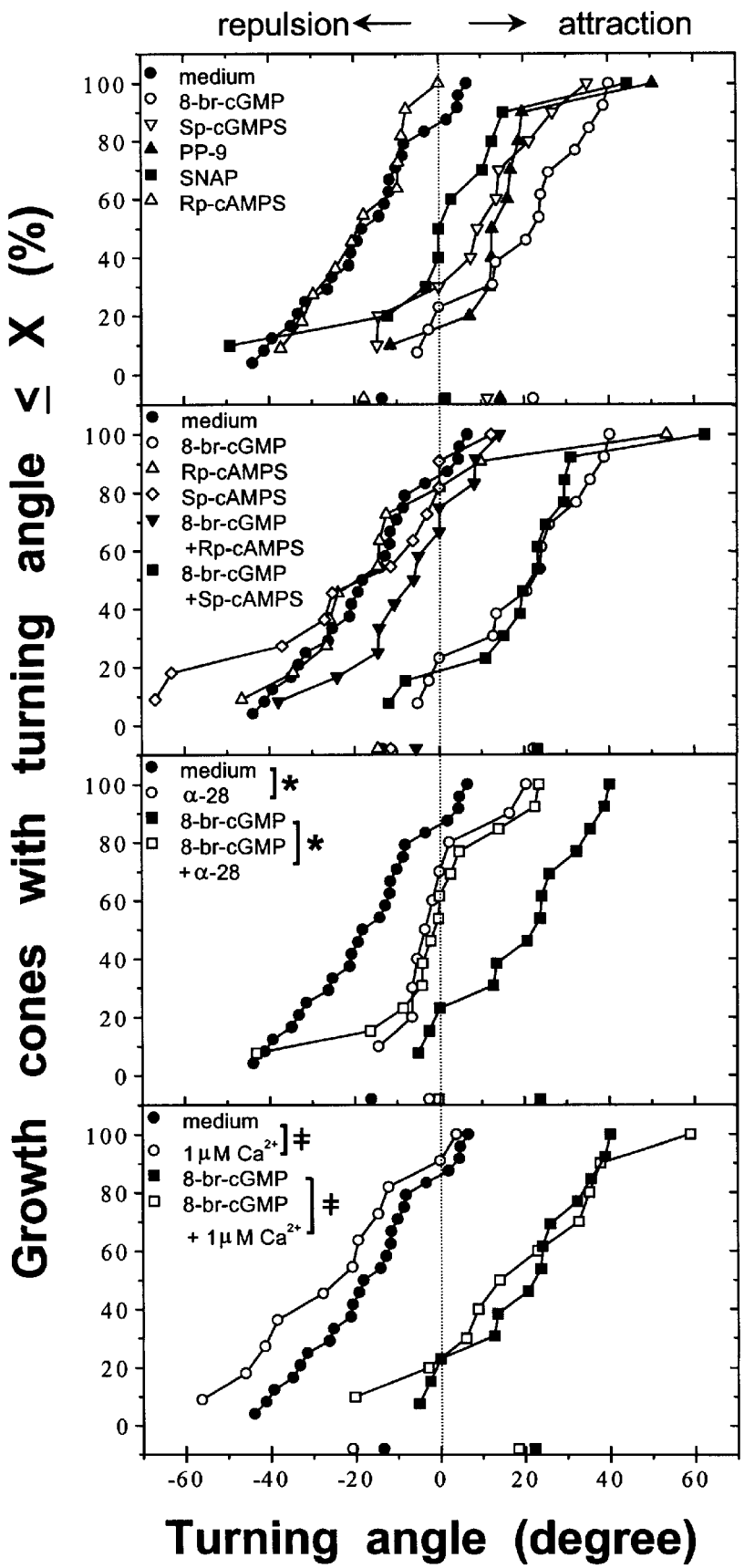

When 8-br-cGMP (10) or Sp-cGMPS (11), membrane permeable agonists of endogenous cGMP signaling pathways, was present in the culture medium (e.g. a gradient of Sema III ~50 μg/ml in the pipette-applied in normal culture medium or in medium containing 100 μM 8-br-cGMP), nearly all growth cones turned toward rather than away from the pipette in the same Sema III gradient (FIG. 2A). Protoporphyrin-9 (PP-9), a guanylate cyclase activator (12), has similar effect (FIG. 2A). Application of a nitric oxide (NO) donor S-Nitroso-N-acetylpenicillamine (SNAP), which activates soluble guanylate cyclase by releasing NO (13), abolished the repulsive turning response without causing a significant attractive response. On the other hand, bath application of Rp-cGMPS (11), a cGMP antagonist and a specific inhibitor of protein kinase G, did not affect the growth cone response. Thus cGMP regulates the direction of growth cone turning induced by Sema III. NO and cGMP can regulate the establishment of the central connections of developing retinal axons and stimulate the synapse formation of developing and regenerating olfactory neurons (14). In contrast to the effect of cGMP analogues, we found that cAMP analogues had no significant effect on the repulsion induced by Sema III gradients (FIG. 2B). However, a cAMW antagonist Rp-cAMPS, but not agonist Sp-cAMPS (15), blocked the conversion of the turning response in the presence of 8-br-cGMP (FIG. 2B), indicating interaction between cAMP- and cGMP-dependent pathways in these neurons.

Figure 1B:
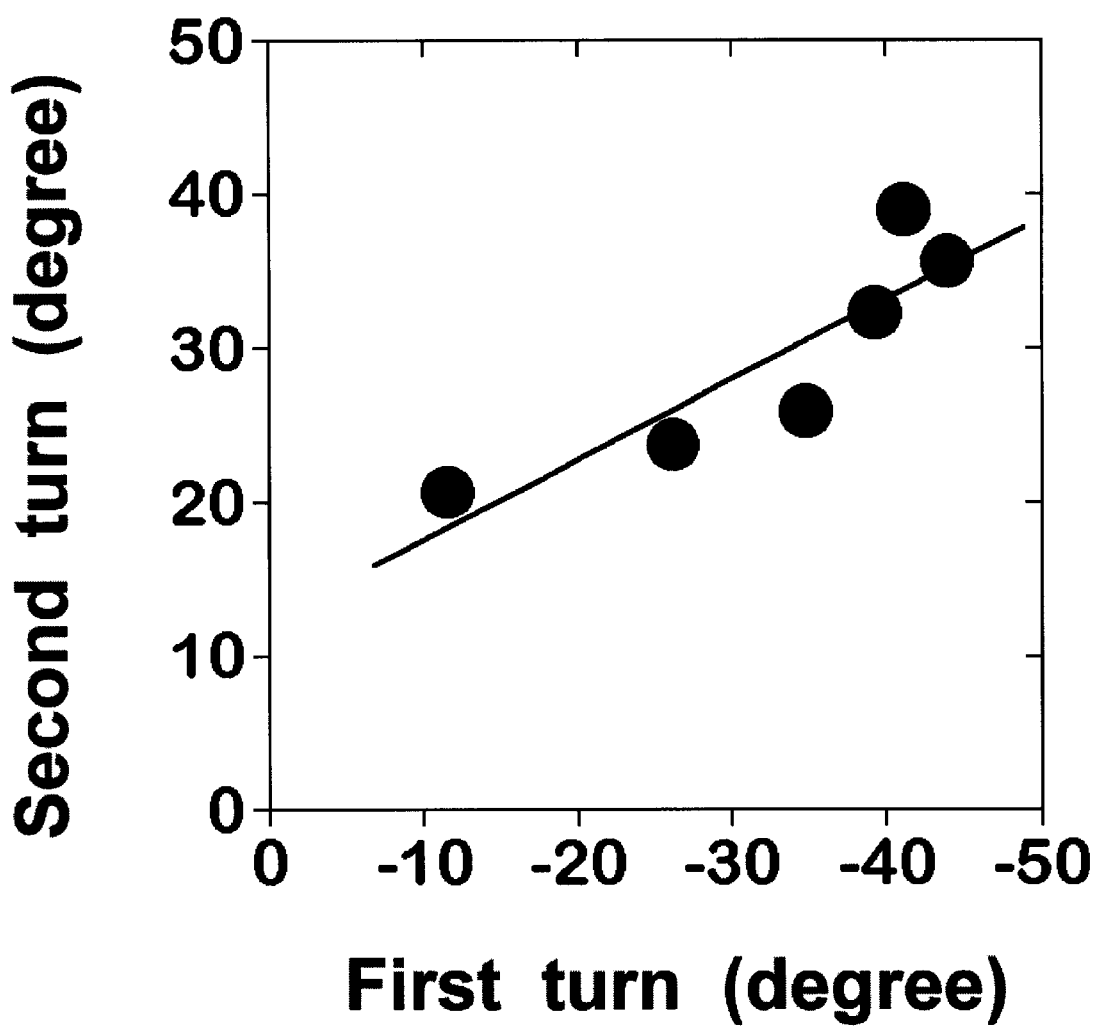

The opposite turning responses are not due to behaviors of different types of neurons in these Xenopus cultures (16), and the turning response can be converted in the same neuron. After a repulsive turning response was first elicited by a Sema III gradient, the same neuron was tested by the same gradient in the presence of 8-br-cGMP (100 μM). We found that the growth cone exhibited an attractive response. Repulsive response was restored after 8-br-cGMP was washed away. Thus the response of the growth cone to a Sema III gradient does not desensitize with time and can be switched between repulsion and attraction in a cGMP-dependent manner. The extent of repulsion versus attraction for each individual neuron appears to be correlated (FIG. 1B), indicating that cGMP affects only the directionality of the response, not the extent to which the growth cone turns.

Neuropilins are receptors for several members of the semaphorin family (17–19), and antibodies against the extracellular domain of neuropilin-1 blocks the effects of Sema III in vitro (17, 18). A function-blocking antiserum to rat neuropilin-1 (α-28) cross-reacts with the Xenopus protein (20). We found that bath application of the α-28 antiserum abolished both the repulsion induced by Sema III under normal conditions and the attraction towards Sema III in the presence of 8-br-cGMP (FIG. 2C). Thus neuropilin-1 function is required for both repulsion and attraction of these growth cones induced by Sema III.

Cyclic nucleotides also change the responsiveness of developing rat dorsal root ganglion (DRG) axons to Sema III. When added to cultures of DRG explants (21), 8-br-cGMP, but not Sp-cAMPS, inhibited the collapsing activity of Sema III in a dose-dependent manner (FIG. 3), while 8-br-cGMP or Sp-cAMPS alone had no detectable effect on growth cones in these cultures. In these experiments higher concentrations of 8-br-cGMP (0.5–5 mM) were needed to inhibit the collapsing activity of Sema III, suggesting that the turning response of Xenopus spinal neurons might be more sensitive to modulation by cGMP than is the collapse of growth cones of rat DRG neurons (9).

Figure 4:
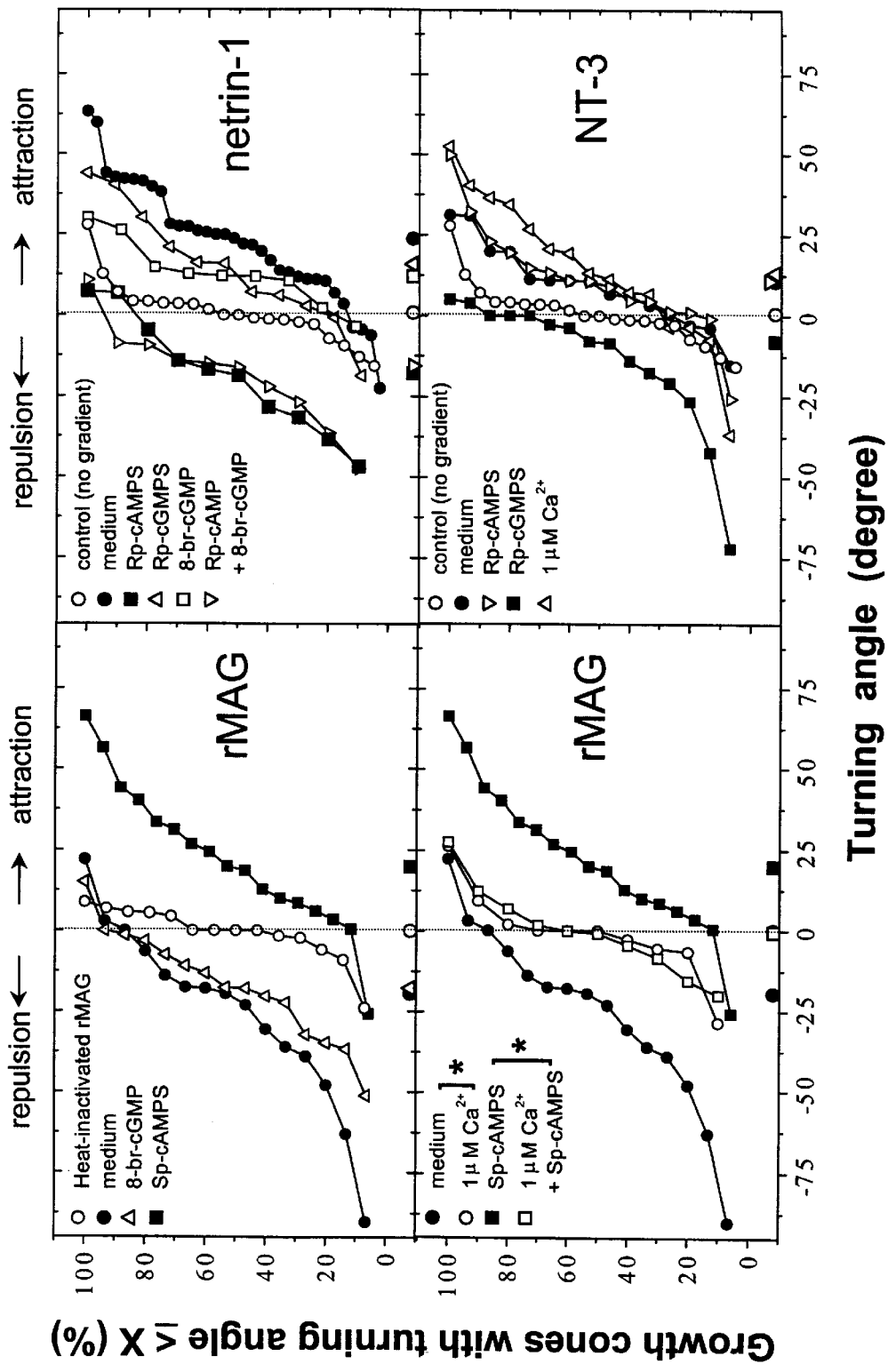

To examine whether the responses to other repulsive factors can be converted, we studied myelin-associated glycoprotein (MAG), a component of myelin and an inhibitor of axonal regeneration (22). A soluble proteolytic fragment of MAG consisting of its extracellular domain is released in abundance from myelin in vivo, and can potently inhibit axon regeneration (23). We found that a gradient of recombinant protein consisting of the extracellular domain of MAG (rMAG) (24) repelled growth cones of Xenopus spinal neurons (FIG. 4A). However, the repulsion by rMAG was not affected by the addition of 8-br-cGMP. On the other hand, when the Sp-cAMPS was added to the medium, the growth cone responses were converted to attraction in the same rMAG gradient (FIG. 4A). Thus the turning response induced by rMAG can be modulated by cAMP-dependent activities. This is reminiscent of the turning responses induced by gradients of BDNF and netrin-1 (4, 5), although the latter factors are normally attractive and are converted to repulsive by inhibition of cAMP-dependent activities.

Cytosolic $Ca^{2+}$ regulates growth cone motility (25). An increase in cytosolic $Ca^{2+}$ levels correlate with growth cone collapse induced by some myelin-associated proteins, but not other factors (26). To examine the involvement of $Ca^{2+}$ in Sema III and rMAG-induced turning, we reduced the extracellular $Ca^{2+}$ concentration ($[Ca^{2+}]_o$) from the normal level of 1 mM to 1 μM (4). This resulted in a 2–3 fold increase in the rate of neurite extension, but no change in the turning responses in a Sema III gradient (FIG. 2D). In contrast, the repulsion and attraction induced by gradients of rMAG were both abolished by the reduction of $[Ca^{2+}]_o$ (FIG. 4B). Thus growth cone turning induced by rMAG, but not Sema III, requires normal $[Ca^{2+}]_o$.

The above studies on growth cone turning induced by Sema III and MAG point to the existence of two distinct pathways involving cAMP and cGMP, with different $Ca^{2+}$-dependences. Growth cone turning induced by BDNF, acetylcholine, and netrin-1, but not NT-3, depends on both $[Ca^{2+}]_o$ and cAMP (4, 5). Here, we found that inhibition or activation of cGMP-dependent pathways by Rp-cGMPS or 8-br-cGMP, respectively, did not affect the attractive turning towards netrin-1 (p>0.1, Kolmogorov-Smirnov test) (FIG. 4C). Moreover, repulsive turning induced by the same netrin-1 gradient in the presence of Rp-cAMPS was also not affected by 8-br-cGMP. On the other hand, the attractive response in a NT-3 gradient was converted to repulsive response by inhibiting cGMP-dependence pathways with Rp-cGMPS, while depletion of $[Ca^{2+}]_o$ or addition of Rp-cAMPS had no effect on the attractive turning (FIG. 4D). Thus, the dependence of turning behavior on $[Ca^{2+}]_o$ for the four factors examined here (rMAG, netrin-1, Sema III and NT-3) correlates with a dependence on cAMP, not cGMP.

In addition to recombinant Collapsin I/Semaphorin III (Sema III) and myelin-associated glycoprotein (rMAG, consisting of the extracellular domain of MAG), we also tested purified myelin-associated glycoprotein (MAG) and myelin (which have many components) and obtained results similar to those with rMAG (see, FIGS. 5–7). For these studies, meylin was made from bovine brain corpus callosum. The tissue was first homogenized. The homogenate then was filtered through a cheese cloth and overlaid on 0.85M sucrose and centrifuged for 25 min at 75,000 g. The material at the interface was collected and resuspended in ice-water and centrifuged for 15 min at 10,000 g. This step was repeated once more, and the purified myelin was collected and washed twice with ice-water. To obtain the soluble form of myelin protein, the myelin fractions were solubilized in 60 mM octylglucoside at 10 mg/ml at 4° C. for 1 hr. The supernatants were collected and dialyzed against PBS and F12 medium. Native MAG was purified from myelin after extraction in 1% octylglucoside and separation by DEAE-Sepharose column as described in McKerracher et al., Neuron 13, 805–811, 1994 and Li et al., Journal of Neuroscience Research, 46, 404–414, 1996.

Studies of the turning response of Xenopus neuronal growth cones induced by a number of diffusible factors (4, 5), including those examined here, have implicated cAMP and cGMP in setting the neuronal response to different guidance cues. The guidance cues examined can all be either attractive or repulsive, depending on the status of cytosolic cyclic nucleotides. Manipulations to increase the level of cyclic nucleotide activity favor attraction and manipulations to de crease the level of cyclic nucleotide activity favor repulsion. Since cyclic nucleotides are known to serve as second messengers for a large number of cell surface receptors (27), the response of a growth cone to a particular guidance cue may thus depend critically on other coincident signals received by the neuron. The susceptibility to conversion between attraction and repulsion may enable a growing axon to respond differentially to the same guidance cue at different points along its journey to its final target (28). The reversal of the action of repulsive factors by elevated cyclic nucleotides provides means for promoting nerve regeneration in the central nervous system (CNS), since effective regeneration in the CNS is blocked by inhibitory factors (22, 29), and modulation of cyclic nucleotide levels helps relieve this inhibition and therefore help stimulate regeneration.

Parenthetical references and notes:

1. R. Keynes and G. M. W. Cook, Cell 83, 161 (1995); M. Tessier-Lavigne and C. S. Goodman, Science 274, 1123 (1996).
2. M. Tessier-Lavigne, M. Placzek, A. G. Lumsden, J. Doss, T. M. Jessell, Nature 336, 775 (1988); N. Ishii, W. G. Wadsworth, B. D. Stern, J. G. Culotti, E. M. Hedgecock, Neuron 9, 873 (1992); T. Serafini et al., Cell 78, 409 (1994); T. E. Kennedy, T. Serafini, J. R. de la Torre, M. Tessier-Lavigne, ibid p. 425; S. A. Colamarino and M. Tessier-Lavigne, ibid 81, 621 (1995).
3. M. Hamelin, Y. Zhou, M.-W. Su, I. M. Scott, J. G. Culotti, Nature 364, 327 (1993).
4. H-j. Song, G-l. Ming, M-m. Poo, ibid 388, 275 (1997).
5. G-l. Ming et al., Neuron 19, 1225 (1997).
6. Y. Luo, D. Raible, J. A. Raper, Cell 75, 217 (1993); A. L. Kolodkin, D. J. Matthes, C. S. Goodman, ibid. p. 1389; E. K. Messersmith et al., ibid. 14, 949 (1995); A. W. Puschel, R. H. Adams, H. Betz, Mole. Cell. Neurosci. 7, 419 (1996).
7. O. Behar, J. A. Golden, H. Mashimo, F. J. Schoen, M. C. Fishman, Nature 383, 525 (1996); M. Taniguchi et al., ibid 19, 519 (1997).
8. Dissociated Xenopus spinal neurons were prepared as described (4,5). Isolated spinal neurons were used for experiments at room temperature (22°–24° C.) 14–22 hour after plating. Sema III was purified from conditioned medium of stable 293-EBNA cell lines secreting Sema III-AP as described (17). To inactivate Sema III activity, the supernatant containing Sema III-AP was heated at 85° C. for 45 minutes [J. Fan and J. A. Raper, Neuron 14, 263 (1995)]. Microscopic gradients of diffusible factors were produced as described (4,5). The average concentration of factors at the growth cone was about $10^3$-fold lower than that in the pipette [A. M. Lohof, M. Quilian, Y. Dan and M-m. Poo, J. Neurosci. 12, 1253 (1992)], and a concentration gradient of 5–10% was created across a growth cone 10 $\mu$m wide, 100 $\mu$m away from the tip of the ejecting pipette. The original direction of neurite growth was defined by the last 10-$\mu$m segment of the neurite. The turning angle was defined by the angle between the original direction of neurite extension and a straight line connecting the positions of the growth cone at the onset and the end of the one hour period. Only growth cones with a net extension >5 $\mu$m over the one-hour period were scored.
9. No obvious collapse of growth cones was observed even when a higher concentration (up to 100 $\mu$g/ml of Sema III in the pipette) was applied to cultured Xenopus spinal neurons. We have not examined whether a uniform concentration of Sema III causes collapse, as it does for chick and rat growth cones.
10. M. A. Schwarzschild and R. E. Zigmond, J. Neurochem. 56, 400 (1991). Pharmacological agents were added to the culture medium at least 30 minutes before the gradient was applied and were present during the experiments. The fmal concentrations of pharmacological agents in the medium were listed.
11. E. Butt, M. van Bemmelen, L. Fischer, U. Walter, B. Jastorff, FEBS Lett. 263, 47 (1990).
12. M. S. Wolin, K. S. Wood, L. J. Ignarro, J. Biol. Chem. 257, 13312 (1982).
13. E. Southam and J. Garthwaite, Neurosci. Lett. 130, 107 (1991).
14. H. H. Wu, C. V. Williams, S. C. McLoon, Science 26, 1593 (1994); A. J. Roskams, D. S. Bredt, T. M. Dawson, G. V. Ronnett, Neuron 13, 289 (1994); S. M. Gibbs and J. W. Truman, Neuron 20, 83 (1998).
15. J. D. Rothermel and L. H. Parker Botelho, J. Biochem. 251, 757 (1988).
16. These Xenopus cultures contain spinal neurons sensitive to various neurotransmitters [J. L. Bixby and N. C. Spitzer, J. Physiol. 353, 143 (1984)] exhibiting a wide-range of capability in secreting acetylcholine [J. Evers, M. Laser, Y. A. Sun, Z. P. Xie, M-m. Poo, *J. Neurosci.* 9, 1523 (1989)]. The variability of turning responses observed within a population of these neurons (see FIG. 2) could be attributed to either the heterogeneity of neuronal types or variability in the cytoplasmic level of cyclic nucleotides or other signal transduction components.

17. Z. He and M. Tessier-Lavigne, *Cell* 90, 739 (1997).
18. A. L. Kolodkin et al., ibid. p. 753.
19. H. Chen, A. Chedotal, Z. He, C. S. Goodman and M. Tessier-Lavigne, *Neuron* 19, 547 (1997).
20. The anti-neuropilin-1 antibody ($\alpha$-28) is directed against the ectodomain of rat neuropilin-1, purified on a protein-A agarose column as described (17), and does not cross-react with neuropilin-2 (19). Using $\alpha$-28, a putative Xenopus neuropilin was detected by Western blot. Interaction of $\alpha$-28 with putative Xenopus neuropilin in cultured Xenopus spinal neurons was confirmed by immunostaining. For antibody blocking experiments, $\alpha$-28 (20 $\mu$g/ml) were added 30 minutes before the onset of the gradient. During the turning assay, the concentration of $\alpha$-28 was 5 $\mu$g/ml.
21. DRG explants derived from E14 rat embryos were cultured with 25 ng/ml NGF on plates precoated with poly-D-lysine and laminin for 20 hours before experiments as described (17). Pharmacological agents were added an hour before the collapse assay. The collapse assay was performed on sensory axons from these explants using Sema III-AP-containing medium essentially as described (17). For visualization, growth cones were stained with rhodaminephalloidin, then washed and mounted.
22. G. Mukhopadhyay, P. Doherty, F. S. Walsh, P. R. Crocker, M. T. Filbin, *Neuron* 13, 757 (1994); L. McKerracher et al., ibid p. 805; M. Schafer, M. Fruttiger, D. Montag, M. Schachner, R. Martini, ibid 16, 1107 (1996).
23. S. Sato, R. H. Quarles, R. O. Brady, W. W. Tourtellotte, *Ann. Neurol.* 15, 264 (1984); S. Tang et al., *Mol. Cell Neurosci.* 9, 333 (1997).
24. To generate rMAG, SF9 cells were infected with baculovirus expressing the extracellular domain of MAG and conditioned medium was collected 5–6 days after infection and purified as described [M. Li et al., *J. Neurosci. Res.* 46, 404 (1996)]. For experiments using inactivated rMAG, rMAG was heated at 80° C. for 35 min.
25. S. B. Kater, M. P. Mattson, C. Cohan, J. A. Conner, *Trends. Neurosci.* 11, 317 (1988). 26. J. K. Ivins, J. A. Raper, R. N. Pittman, *J. Neurosci.* 11, 1597 (1991); C. E. Bandtlow, M. F. Schmidt, T. D. Hassinger, M. E. Schwab, S. B. Kater, *Science* 259, 80 (1993); J. Loschinger et al., *J. Neurobiol.* 33, 825 (1997).
27. J. R. Cooper, F. E. Bloom, R. H. Roth, *The Biochemical Basis of Neuropharmacology* (7th ed, Oxford University Press, New York, 1996); R. Laufer and J. Changeux, *EMBO J.* 6, 901 (1987); J. H. Fong and D. E. Ingber, *Biochem. Biophys. Res. Commun.* 221, 19 (1996).
28. Attraction of commissural axons towards the floor plate in the developing spinal cord might be switched off (or even converted to a repulsive response) after the contact with the floor plate cells, allowing fuirther axonal growth past the floor plate [see R. Shirasaki, R. Katsumata, F. Murakami, *Science* 279, 105 (1998)].
29. M. E. Schwab and D. Bartholdi, *Physiol. Rev.* 76, 319 (1996).

What is claimed is:

1. A method for promoting growth of a mammalian central nervous system neural cell subject to growth inhibition by an endogenous neural cell growth repulsion factor, the method comprising the steps of contacting the cell with an effective amount of an activator of a cyclic nucleotide dependent protein kinase, whereby the growth of the cell is promoted, and detecting a resultant promotion of the growth of the cell.

2. The method of claim 1 consisting essentially of the contacting and detecting steps.

3. The method of claim 2, wherein the activator comprises an active component selected from a cyclic nucleotide analog, an activator of a cyclic nucleotide cyclase, a nitric oxide (NO) inducer and an inhibitor of a cyclic nucleotide phosphodiesterase.

4. The method of claim 2, wherein the activator comprises an active component selected from:
   (a) a cyclic nucleotide analog selected from an adenylate cyclase activator selected from forskolin, 7$\beta$-deaceyl-7$\beta$-[$\gamma$-(morpholino)butyryl]-forskolin and 6$\beta$-[$\beta$'-(piperidino)-propionyl]-forskolin; and a guanylate cyclase activator which is protoporphyrin-9 (PP-9);
   (b) an activator of a cyclic nucleotide cyclase selected from a protein kinase-A (PKA) activator selected from 8-bromo-adenosine 3',5'-monophosphate (8-Br-cAMP), 8-chloro-adenosine 3',5'-monophosphate (8-Cl-cAMP), 8-(4-chlorophenylthio)-cAMP, dibutyryl-cAMP, dioctanoyl-cAMP, Sp-cAMPS and Sp-8-bromo-cAMPS; and a protein kinase G (PKG) activator selected from 8-br-cGMP, 8-(4-chlorophenylthio)-cGMP and dibutyryl-cGMP;
   (c) a NO inducer which is an NO donor selected from S-nitroso-N-acetylpenicillamine (SNAP), Glyco-SNAP-1, Glyco-SNAP-2,2,2'-(hydroxynitrosohydrazono)bis-ethanamine (NOC-18) and (+/−)-(E)-4-ethyl-2-[(E)-hydroxyimino]-5-nitro-3-hexenamide (NOR-3); and
   (d) an inhibitor of a cyclic nucleotide phosphodiesterase selected from 3-isobutyl-1-methylxanthine (IBMX) and rolipram.

5. The method of claim 2, wherein the activator comprises an active component that is forskolin.

6. The method of claim 2, wherein the activator comprises an active component that is 7$\beta$-deaceyl-7$\beta$-[$\gamma$-(morpholino) butyryl]-forskolin.

7. The method of claim 2, wherein the activator comprises an active component that is 6$\beta$-[$\beta$'-(piperidino)-propionyl]-forskolin.

8. The method of claim 2, wherein the activator comprises an active component that is protoporphyrin-9 (PP-9).

9. The method of claim 2, wherein the activator comprises an active component that is 8-bromo-adenosine 3',5'-monophosphate (8-Br-cAMP).

10. The method of claim 2, wherein the activator comprises an active component that is 8-chloro-adenosine 3',5'-monophosphate (8-Cl-cAMP).

11. The method of claim 2, wherein the activator comprises an active component that is 8-(4-chlorophenylthio)-cAMP.

12. The method of claim 2, wherein the activator comprises an active component that is dibutyryl-cAMP.

13. The method of claim 2, wherein the activator comprises an active component that is dioctanoyl-cAMP.

14. The method of claim 2, wherein the activator comprises an active component that is Sp-cAMPS.

15. The method of claim 2, wherein the activator comprises an active component that is Sp-8-bromo-cAMPS.

16. The method of claim 2, wherein the activator comprises an active component that is 8-br-cGMP.

17. The method of claim 2, wherein the activator comprises an active component that is 8-(4-chlorophenylthio)-cGMP.

18. The method of claim 2, wherein the activator comprises an active component that is dibutyryl-cGMP.

19. The method of claim 2, wherein the activator comprises an active component that is S-nitroso-N-acetylpenicillamine (SNAP).

20. The method of claim 2, wherein the activator comprises an active component that is Glyco-SNAP-1.

21. The method of claim 2, wherein the activator comprises an active component that is Glyco-SNAP-2.

22. The method of claim 2, wherein the activator comprises an active component that is 2,2'-(hydroxynitrosohydrazono)bis-ethanamine (NOC-18).

23. The method of claim 2, wherein the activator comprises an active component that is (+/−)-(E)-4-ethyl-2-[(E)-hydroxyimino]-5-nitro-3-hexenamide (NOR-3).

24. The method of claim 2, wherein the activator comprises an active component that is 3-isobutyl-1-methylxanthine (IBMX).

25. The method of claim 2, wherein the activator comprises an active component that is rolipram.

26. The method of claim 2, wherein the repulsion factor comprises an active component selected from a semaphorin, a netrin, a MAG and a CNS myelin fraction.

27. The method of claim 2, wherein the protein kinase is protein kinase A or G.

28. The method of claim 2, wherein the cell is a corticospinal tract neuron.

29. The method of claim 2, wherein the contacting step is for up to one hour.

30. The method of claim 2, wherein the contacting step is for up to 30 minutes.

31. The method of claim 1, wherein the contacting step comprises locally administering to a human patient in need thereof at an axon of the cell a therapeutically effective amount of the activator of a cyclic nucleotide dependent protein kinase, whereby growth of the axon is promoted; and the detecting step comprises detecting a resultant promotion of the axon.

32. The method of claim 31 consisting essentially of the contacting and detecting steps.

33. The method of claim 32, wherein the activator comprises an active component selected from a cyclic nucleotide analog, an activator of a cyclic nucleotide cyclase, a nitric oxide (NO) inducer and an inhibitor of a cyclic nucleotide phosphodiesterase.

34. The method of claim 32, wherein the activator comprises an active component selected from:

(a) a cyclic nucleotide analog selected from an adenylate cyclase activator selected from forskolin, 7β-deaceyl-7β-[γ-(morpholino)butyryl]-forskolin and 6β-[β'-(piperidino)-propionyl]-forskolin; and a guanylate cyclase activator which is protoporphyrin-9 (PP-9);

(b) an activator of a cyclic nucleotide cyclase selected from a protein kinase-A (PKA) activator selected from 8-bromo-adenosine 3',5'-monophosphate (8-Br-cAMP), 8-chloroadenosine 3',5'-monophosphate (8-Cl-cAMP), 8-(4-chlorophenylthio)-cAMP, dibutyryl-cAMP, dioctanoyl-cAMP, Sp-cAMPS and Sp-8-bromo-cAMPS; and a protein kinase G (PKG) activator selected from 8-br-cGMP, 8-(4-chlorophenylthio)-cGMP and dibutyryl-cGMP;

(c) a NO inducer which is an NO donor selected from S-nitroso-N-acetylpenicillamine (SNAP), Glyco-SNAP-1, Glyco-SNAP-2,2,2'-(hydroxynitrosohydrazono)bis-ethanamine (NOC-18) and (+/−)-(E)-4-ethyl-2-[(E)-hydroxyimino]-5-nitro-3-hexenamide (NOR-3); and (d) an inhibitor of a cyclic nucleotide phosphodiesterase selected from 3-isobutyl-1-methylxanthine (IBMX) and rolipram.

35. The method of claim 32, wherein the activator comprises an active component that is forskolin.

36. The method of claim 32, wherein the activator comprises an active component that is 7β-deaceyl-7β-[γ-(morpholino)butyryl]-forskolin.

37. The method of claim 32, wherein the activator comprises an active component that is 6β-[β'-(piperidino)-propionyl]-forskolin.

38. The method of claim 32, wherein the activator comprises an active component that is protoporphyrin-9 (PP-9).

39. The method of claim 32, wherein the activator comprises an active component that is 8-bromo-adenosine 3',5'-monophosphate (8-Br-cAMP).

40. The method of claim 32, wherein the activator comprises an active component that is 8-chloro-adenosine 3',5'-monophosphate (8-Cl-cAMP).

41. The method of claim 32, wherein the activator comprises an active component that is 8-(4-chlorophenylthio)-cAMP.

42. The method of claim 32, wherein the activator comprises an active component that is dibutyryl-cAMP.

43. The method of claim 32, wherein the activator comprises an active component that is dioctanoyl-cAMP.

44. The method of claim 32, wherein the activator comprises an active component that is Sp-cAMPS.

45. The method of claim 32, wherein the activator comprises an active component that is Sp-8-bromo-cAMPS.

46. The method of claim 32, wherein the activator comprises an active component that is 8-br-cGMP.

47. The method of claim 32, wherein the activator comprises an active component that is 8-(4-chlorophenylthio)-cGMP.

48. The method of claim 32, wherein the activator comprises an active component that is dibutyryl-cGMP.

49. The method of claim 32, wherein the activator comprises an active component that is S-nitroso-N-acetylpenicillamine (SNAP).

50. The method of claim 32, wherein the activator comprises an active component that is Glyco-SNAP-1.

51. The method of claim 32, wherein the tivator comprises an active component that is Glyco-SNAP-2.

52. The method of claim 32, wherein the activator comprises an active component that is 2,2'-(hydroxynitrosohydrazono)bis-ethanamine (NOC-18).

53. The method of claim 32, wherein the activator comprises an active component that is (+/−)-(E)-4-ethyl-2-[(E)-hydroxyimino]-5-nitro-3-hexenamide (NOR-3).

54. The method of claim 32, wherein the activator comprises an active component that is 3-isobutyl-1-methylxanthine (IBMX).

55. The method of claim 32, wherein the activator comprises an active component that is rolipram.

56. The method of claim 32, wherein the repulsion factor comprises an active component selected from a semaphorin, a netrin, a MAG and a CNS myelin fraction.

57. The method of claim 32, wherein the protein kinase is protein kinase A or G.

58. The method of claim 32, wherein the cell is a corticospinal tract neuron damaged by a spinal injury.

59. The method of claim 34, wherein the cell is a corticospinal tract neuron damaged by a spinal injury.

60. The method of claim 32, wherein the contacting step is for up to one hour.

61. The method-of claim 32, wherein the contacting step is for up to 30 minutes.

62. An in vitro mixture comprising a mammalian central nervous system neural cell, a predetermined amount of an activator of a cyclic nucleotide dependent protein kinase and a neural cell growth repulsion factor, wherein the cell is subject to growth inhibition by the neural cell growth repulsion factor.

63. The mixture of claim 62, wherein the activator comprises an active component selected from:

(a) a cyclic nucleotide analog selected from an adenylate cyclase activator selected from forskolin, 7β-deaceyl-7β-[γ-(morpholino)butyryl]-forskolin and 6β-[β'-(piperidino)-propionyl]-forskolin; and a guanylate cyclase activator which is protoporphyrin-9 (PP-9);

(b) an activator of a cyclic nucleotide cyclase selected from a protein kinase-A (PKA) activator selected from 8-bromo-adenosine 3',5'-monophosphate (8-Br-cAMP), 8-chloro-adenosine 3',5'-monophosphate (8-Cl-cAMP), 8-(4-chlorophenylthio)-cAMP, dibutyryl-cAMP, dioctanoyl-cAMP, Sp-cAMPS and Sp-8-bromo-cAMPS; and a protein kinase G (PKG) activator selected from 8-br-cGMP, 8-(4-chlorophenylthio)-cGMP and dibutyryl-cGMP;

(c) a NO inducer which is an NO donor selected from S-nitroso-N-acetylpenicillamine (SNAP), Glyco-SNAP-1, Glyco-SNAP-2,2,2'-(hydroxynitrosohydrazono)bis-ethanamine (NOC-18) and (+/−)-(E)-4-ethyl-2-[(E)-hydroxyimino]-5-nitro-3-hexenamide (NOR-3); and (d) an inhibitor of a cyclic nucleotide phosphodiesterase selected from 3-isobutyl-1-methylxanthine (IBMX) and rolipram.

64. The mixture of claim 62, wherein the cell is a corticospinal tract neuron.

* * * * *

UNITED STATES PATENT AND TRADEMARK OFFICE
CERTIFICATE OF CORRECTION

PATENT NO.   : 6,268,352 B1
DATED        : July 31, 2001
INVENTOR(S)  : Hong-jun Song et al.

It is certified that error appears in the above-identified patent and that said Letters Patent is hereby corrected as shown below:

Please correct claims 4, 34 and 63 of this Patent to read as follows:

Column 4,
Lines 11-35:
4.      The method of claim 2, wherein the activator comprises an active component selected from:
    (a) an activator of a cyclic nucleotide cyclase selected from an adenylate cyclase activator selected from forskolin, 7β-deaceyl-7β-[γ-(morpholino)butyryl]-forskolin and 6β-[β'-(piperidino)- propionyl]-forskolin; and a guanylate cyclase activator which is protoporphyrin-9(PP-9);
    (b) a cyclic nucleotide analog selected from a protein kinase-A (PKA) activator selected from 8-bromo-adenosine 3',5'-monophosphate (8-Br-cAMP), 8-chloro-adenosine 3',5'-monophosphate (8-Cl-cAMP), 8-(4-chlorophenylthio)-cAMP, dibutyryl-cAMP, dioctanoyl-cAMP, Sp-cAMPS and Sp-8-bromo-cAMPS; and a protein kinase G (PKG) activator selected from 8-br-cGMP, 8-(4-chlorophenylthio)-cGMP and dibutyryl-cGMP;
    (c) a NO inducer which is an NO donor selected from S-nitroso-N-acetylpenicillamine (SNAP), Glyco-SNAP-1, Glyco-SNAP-2, 2,2'-(hydroxynitrosohydrazono)bis-ethanamine (NOC-18) and (+/-)-(E)-4-ethyl-2-[(E)-hydroxyimino]-5-nitro-3-hexenamide (NOR-3); and
    (d) an inhibitor of a cyclic nucleotide phosphodiesterase selected from 3-isobutyl-l-methylxanthine (IBMX) and rolipram.

Column 13, line 46 to Column 14, lines 1-3:
34.     The method of claim 32, wherein the activator comprises an active component selected from:
    (a) an activator of a cyclic nucleotide cyclase selected from an adenylate cyclase activator selected from forskolin, 7β-deaceyl-7β-[γ-(morpholino)butyryl-forskolin and 6β-[β'-(piperidino)- propionyl]-forskolin; and a guanylate cyclase activator which is protoporphyrin-9(PP-9);

UNITED STATES PATENT AND TRADEMARK OFFICE
CERTIFICATE OF CORRECTION

PATENT NO. : 6,268,352 B1
DATED : July 31, 2001
INVENTOR(S) : Hong-jun Song et al.

It is certified that error appears in the above-identified patent and that said Letters Patent is hereby corrected as shown below:

Column 13, line 46, to Column 14, lines 1-3 cont'd:
    (b) a cyclic nucleotide analog selected from a protein kinase-A (PKA) activator selected from 8-bromo-adenosine 3',5'-monophosphate (8-Br-cAMP), 8-chloro-adenosine 3',5'-monophosphate (8-Cl-cAMP), 8-(4-chlorophenylthio)-cAMP, dibutyryl-cAMP, dioctanoyl-cAMP, Sp-cAMPS and Sp-8-bromo-cAMPS; and a protein kinase G (PKG) activator selected from 8-br-cGMP, 8-(4-chlorophenylthio)-cGMP and dibutyryl-cGMP;
    (c) a NO inducer which is an NO donor selected from S-nitroso-N-acetylpenicillamine (SNAP), Glyco-SNAP-1, Glyco-SNAP-2, 2,2'-(hydroxynitrosohydrazono)bis-ethanamine (NOC-18) and (+/-)-(E)-4-ethyl-2-[(E)-hydroxyimino]-5-nitro-3-hexenamide (NOR-3); and
    (d) an inhibitor of a cyclic nucleotide phosphodiesterase selected from 3-isobutyl-l-methylxanthine (IBMX) and rolipram.

Column 15, line 7 to Column 16, lines 1-14:
63.     The mixture of claim 62, wherein the activator comprises an active component selected from:
    (a) an activator of a cyclic nucleotide cyclase selected from an adenylate cyclase activator selected from forskolin, 7β-deaceyl-7β-[γ-(morpholino)butyrly]-forskolin and 6β-[β'-(piperidino)- propionyl]-forskolin; and a guanylate cyclase activator which is protoporphyrin-9(PP-9);
    (b) a cyclic nucleotide analog selected from a protein kinase-A (PKA) activator selected from 8-bromo-adenosine 3',5'-monophosphate (8-Br-cAMP), 8-chloro-adenosine 3',5'-monophosphate (8-Cl-cAMP), 8-(4-chlorophenylthio)-cAMP, dibutyryl-cAMP, dioctanoyl-cAMP, Sp-cAMPS and Sp-8-bromo-cAMPS; and a protein kinase G (PKG) activator selected from 8-br-cGMP, 8-(4-chlorophenylthio)-cGMP and dibutyryl-cGMP;
    (c) a NO inducer which is an NO donor selected from S-nitroso-N-acetylpenicillamine (SNAP), Glyco-SNAP-1, Glyco-SNAP-2, 2,2'-(hydroxynitrosohydrazono)bis-ethanamine (NOC-18) and (+/-)-(E)-4-ethyl-2-[(E)-hydroxyimino]-5-nitro-3-hexenamide (NOR-3); and

UNITED STATES PATENT AND TRADEMARK OFFICE
CERTIFICATE OF CORRECTION

PATENT NO.    : 6,268,352 B1
DATED         : July 31, 2001
INVENTOR(S)   : Hong-jun Song et al.

It is certified that error appears in the above-identified patent and that said Letters Patent is hereby corrected as shown below:

<u>Column 15, line 7 to Column 16, lines 1-14 cont'd:</u>
    (d) an inhibitor of a cyclic nucleotide phosphodiesterase selected from 3-isobutyl-l-methylxanthine (IBMX) and rolipram.

Signed and Sealed this

Twenty-sixth Day of November, 2002

*Attest:*

*Attesting Officer*

JAMES E. ROGAN
*Director of the United States Patent and Trademark Office*